United States Patent
Young, Jr. et al.

(10) Patent No.: US 6,864,973 B2
(45) Date of Patent: Mar. 8, 2005

(54) METHOD AND APPARATUS TO PRE-SCAN AND PRE-TREAT FILM FOR IMPROVED DIGITAL FILM PROCESSING HANDLING

(75) Inventors: Robert S. Young, Jr., Austin, TX (US); George G. Mooty, Austin, TX (US); Michael R. Thering, Austin, TX (US)

(73) Assignee: Eastman Kodak Company, Rochester, NY (US)

( * ) Notice: Subject to any disclaimer, the term of this patent is extended or adjusted under 35 U.S.C. 154(b) by 637 days.

(21) Appl. No.: 09/751,119

(22) Filed: Dec. 28, 2000

(65) Prior Publication Data

US 2002/0018201 A1 Feb. 14, 2002

Related U.S. Application Data

(60) Provisional application No. 60/173,648, filed on Dec. 30, 1999.

(51) Int. Cl.[7] ............................................. G01N 21/000
(52) U.S. Cl. ..................................................... 356/239.2
(58) Field of Search ................................. 356/600–613, 356/237.1–237.6, 239.1–239.8, 238.1–238.3; 250/559.02–559.05, 559.45–559.46

(56) References Cited

U.S. PATENT DOCUMENTS

| | | | |
|---|---|---|---|
| 2,404,138 A | 10/1946 | Mayer ............................ | 95/94 |
| 3,520,689 A | 7/1970 | Nagae et al. ................... | 96/55 |
| 3,520,690 A | 7/1970 | Nagae et al. ................... | 96/55 |
| 3,587,435 A | 6/1971 | Chioffe .......................... | 95/89 |
| 3,615,479 A | 10/1971 | Kohler et al. .................. | 96/48 |
| 3,615,498 A | 10/1971 | Aral .............................. | 96/55 |
| 3,617,282 A | 11/1971 | Bard ............................. | 96/59 |
| 3,747,120 A | 7/1973 | Stemme ........................ | 346/75 |
| 3,825,755 A * | 7/1974 | Ruskin ................. | 250/339.11 |
| 3,903,541 A | 9/1975 | Von Meister et al. ....... | 354/317 |

(List continued on next page.)

FOREIGN PATENT DOCUMENTS

| | | | |
|---|---|---|---|
| EP | 0 261 782 A2 | 8/1987 | ............ H04N/1/46 |
| EP | 0 422 220 A1 | 3/1989 | ............ A61B/6/03 |
| EP | 0 482 790 B1 | 9/1991 | ............ H04N/1/40 |
| EP | 0 525 886 A3 | 7/1992 | ............ G03D/5/00 |
| EP | 0 580 293 A1 | 6/1993 | ............ H04N/1/04 |

(List continued on next page.)

OTHER PUBLICATIONS

"Adaptive Fourier Threshold Filtering: A Method to Reduce Noise and Incoherent Artifacts in High Resolution Cardiac Images", Doyle, M., et al., 8306 Magnetic Resonance in Medicine 31, No. 5, Baltimore, MD, May, pp. 546–550, 1994.

(List continued on next page.)

Primary Examiner—Tu T. Nguyen
(74) Attorney, Agent, or Firm—Dinsmore + Shohl; David A. Novais

(57) ABSTRACT

The present invention provides a method, apparatus and system that pre-scans and pre-treats film for improved digital film processing. The apparatus for use with the invention includes, generally, a sensor for detecting one or more imperfections on the film and a microprocessor connected to the sensor that determines the amount and extent of imperfections of the film based on one or more reference readings. The present invention may also include a tape dispenser, cleaning rollers, a blower or vacuum to remove and/or correct any imperfections in the film. One embodiment includes a cleaning system for a particle removal member which removes particles from film. The cleaning system is relatively movable and selectively contactable with the particle removal member to clean particles from the particle removal member.

33 Claims, 4 Drawing Sheets

U.S. PATENT DOCUMENTS

| | | | |
|---|---|---|---|
| 3,946,398 A | 3/1976 | Kyser et al. | 346/1 |
| 3,959,048 A | 5/1976 | Stanfield et al. | |
| 4,026,756 A | 5/1977 | Stanfield et al. | |
| 4,081,577 A | 3/1978 | Horner | 427/424 |
| 4,142,107 A | 2/1979 | Hatzakis et al. | 250/571 |
| 4,215,927 A | 8/1980 | Grant et al. | 354/317 |
| 4,249,985 A | 2/1981 | Stanfield | |
| 4,301,469 A | 11/1981 | Modeen et al. | 358/75 |
| 4,490,729 A | 12/1984 | Clark et al. | 346/75 |
| 4,501,480 A | 2/1985 | Matsui et al. | 354/298 |
| 4,564,280 A | 1/1986 | Fukuda | 354/317 |
| 4,594,598 A | 6/1986 | Iwagami | 346/140 |
| 4,621,037 A | 11/1986 | Kanda et al. | 430/30 |
| 4,623,236 A | 11/1986 | Stella | 354/318 |
| 4,636,808 A | 1/1987 | Herron | 346/75 |
| 4,666,307 A | 5/1987 | Matsumoto et al. | 356/404 |
| 4,670,779 A | 6/1987 | Nagano | 358/75 |
| 4,687,943 A * | 8/1987 | Bowen et al. | 250/570 |
| 4,736,221 A | 4/1988 | Shidara | 354/317 |
| 4,745,040 A | 5/1988 | Levine | 430/21 |
| 4,755,844 A | 7/1988 | Tsuchiya et al. | 354/317 |
| 4,777,102 A | 10/1988 | Levine | 430/21 |
| 4,796,061 A | 1/1989 | Ikeda et al. | |
| 4,814,630 A | 3/1989 | Lim | 250/578 |
| 4,821,114 A | 4/1989 | Gebhardt | 358/75 |
| 4,845,551 A | 7/1989 | Matsumoto | 358/80 |
| 4,851,311 A | 7/1989 | Millis et al. | 430/30 |
| 4,857,430 A | 8/1989 | Millis et al. | 430/30 |
| 4,875,067 A | 10/1989 | Kanzaki et al. | 354/325 |
| 4,969,045 A | 11/1990 | Haruki et al. | 358/228 |
| 4,994,918 A | 2/1991 | Lingemann | |
| 5,034,767 A | 7/1991 | Netz et al. | 354/317 |
| 5,101,286 A | 3/1992 | Patton | 358/487 |
| 5,124,216 A | 6/1992 | Giapis et al. | 430/30 |
| 5,155,596 A | 10/1992 | Kurtz et al. | 358/214 |
| 5,196,285 A | 3/1993 | Thomson | 430/30 |
| 5,212,512 A | 5/1993 | Shiota | 354/319 |
| 5,231,439 A | 7/1993 | Takahashi et al. | 354/313 |
| 5,235,352 A | 8/1993 | Pies et al. | 346/140 |
| 5,255,408 A | 10/1993 | Blackman | |
| 5,266,805 A | 11/1993 | Edgar | 250/330 |
| 5,267,030 A | 11/1993 | Giorgianni et al. | 358/527 |
| 5,292,605 A | 3/1994 | Thomson | 430/30 |
| 5,296,923 A | 3/1994 | Hung | 358/527 |
| 5,350,651 A | 9/1994 | Evans et al. | 430/21 |
| 5,350,664 A | 9/1994 | Simons | 430/362 |
| 5,357,307 A | 10/1994 | Glanville et al. | 354/324 |
| 5,360,701 A | 11/1994 | Elton et al. | |
| 5,371,542 A | 12/1994 | Pauli et al. | 348/262 |
| 5,391,443 A | 2/1995 | Simons et al. | 430/21 |
| 5,414,779 A | 5/1995 | Mitch | 382/199 |
| 5,416,550 A | 5/1995 | Skye et al. | 354/298 |
| 5,418,119 A | 5/1995 | Simons | 430/507 |
| 5,418,597 A | 5/1995 | Lahcanski et al. | |
| 5,432,579 A | 7/1995 | Tokuda | 354/293 |
| 5,436,738 A | 7/1995 | Manico | 358/503 |
| 5,440,365 A | 8/1995 | Gates et al. | 354/298 |
| 5,447,811 A | 9/1995 | Buhr et al. | 430/20 |
| 5,448,380 A | 9/1995 | Park | 358/520 |
| 5,452,018 A | 9/1995 | Capitant et al. | 348/651 |
| 5,465,155 A | 11/1995 | Edgar | 358/500 |
| 5,496,669 A | 3/1996 | Pforr et al. | 430/22 |
| 5,516,608 A | 5/1996 | Hobbs et al. | 430/30 |
| 5,519,510 A | 5/1996 | Edgar | |
| 5,546,477 A | 8/1996 | Knowles et al. | 382/242 |
| 5,550,566 A | 8/1996 | Hodgson et al. | 345/202 |
| 5,552,904 A | 9/1996 | Ryoo et al. | 358/518 |
| 5,563,717 A | 10/1996 | Koeng et al. | 358/406 |
| 5,568,270 A | 10/1996 | Endo | 358/298 |
| 5,576,836 A | 11/1996 | Sano et al. | 358/302 |
| 5,581,376 A | 12/1996 | Harrington | 358/518 |
| 5,596,415 A | 1/1997 | Cosgrove et al. | 358/296 |
| 5,627,016 A | 5/1997 | Manico | 430/434 |
| 5,641,971 A * | 6/1997 | Prigent | 250/559.02 |
| 5,664,253 A | 9/1997 | Meyers | 396/603 |
| 5,664,255 A | 9/1997 | Wen | 396/627 |
| 5,667,944 A | 9/1997 | Reem et al. | 430/359 |
| 5,678,116 A | 10/1997 | Sugimoto et al. | 369/611 |
| 5,691,118 A | 11/1997 | Haye | 430/357 |
| 5,695,914 A | 12/1997 | Simon et al. | 430/379 |
| 5,698,382 A | 12/1997 | Nakahanada et al. | 430/418 |
| 5,726,773 A | 3/1998 | Mehlo et al. | 358/474 |
| 5,739,897 A | 4/1998 | Frick et al. | 355/40 |
| 5,771,107 A | 6/1998 | Fujimoto et al. | 358/464 |
| 5,790,277 A | 8/1998 | Edgar | |
| 5,835,811 A | 11/1998 | Tsumura | 396/598 |
| 5,870,172 A | 2/1999 | Blume | 355/27 |
| 5,880,819 A | 3/1999 | Tanaka et al. | |
| 5,892,595 A | 4/1999 | Yamakawa et al. | 358/530 |
| 5,930,388 A | 7/1999 | Murakami et al. | 382/167 |
| 5,963,662 A | 10/1999 | Vachtsevanos et al. | 382/150 |
| 5,966,465 A | 10/1999 | Keith et al. | 382/232 |
| 5,979,011 A | 11/1999 | Miyawaki et al. | |
| 5,982,936 A | 11/1999 | Tucker et al. | 382/233 |
| 5,982,937 A | 11/1999 | Accad | 382/239 |
| 5,982,941 A | 11/1999 | Loveridge et al. | 382/260 |
| 5,982,951 A | 11/1999 | Katayama et al. | 382/284 |
| 5,988,896 A | 11/1999 | Edgar | |
| 5,991,444 A | 11/1999 | Burt et al. | 382/232 |
| 5,998,109 A | 12/1999 | Hirabayashi | 430/434 |
| 6,000,284 A | 12/1999 | Shin et al. | |
| 6,005,987 A | 12/1999 | Nakamura et al. | 382/294 |
| 6,065,824 A | 5/2000 | Bullock et al. | 347/19 |
| 6,069,714 A | 5/2000 | Edgar | 358/487 |
| 6,089,687 A | 7/2000 | Helterline | 347/7 |
| 6,101,273 A | 8/2000 | Matama | 382/169 |
| 6,102,508 A | 8/2000 | Cowger | 347/7 |
| 6,137,965 A | 10/2000 | Burgeios et al. | 396/626 |

FOREIGN PATENT DOCUMENTS

| | | | |
|---|---|---|---|
| EP | 0 669 753 A2 | 2/1995 | H04N/1/407 |
| EP | 0 794 454 A2 | 2/1997 | G03B/27/73 |
| EP | 0 930 498 A2 | 12/1998 | G01N/21/88 |
| WO | WO 90/01240 | 2/1990 | H04N/1/40 |
| WO | WO 91/09493 | 6/1991 | H04N/5/217 |
| WO | WO 97/25652 | 7/1997 | G03D/5/00 |
| WO | WO 9743613 | 11/1997 | |
| WO | WO 9819216 | 5/1998 | |
| WO | WO 9825399 | 6/1998 | |
| WO | WO 9831142 | 7/1998 | |
| WO | WO 9834157 | 8/1998 | |
| WO | WO 98/34157 | 8/1998 | |
| WO | WO 9834397 | 8/1998 | |
| WO | WO 99/43148 | 8/1999 | H04N/1/00 |
| WO | WO 01/01197 | 1/2001 | G03D/5/00 |
| WO | WO 01/13174 A1 | 2/2001 | G03D/5/06 |

OTHER PUBLICATIONS

"Anisotropic Spectral Magnitude Estimation Filters for Noise Reduction and Image Enhancement", Aich, T., et al., Philips GmbH Research Laboratories, IEEE, pp. 335–338, 1996.

"Adaptive–neighborhood filtering of images corrupted by signal–dependent noise", Rangayyan, R., et al., Applied Optics, vol. 37, No. 20, pp. 4477–4487, Jul. 10, 1998.

"Grayscale Characteristics", The Nature of Color Images, Photographic Negatives, pp. 163–168.

"Parallel Production of Oligonucleotide Arrays Using Membranes and Reagent Jet Printing", Stimpson, D., et al., Research Reports, BioTechniques, vol. 25, No. 5, pp. 886–890, 1998.

"Low–Cost Display Assembly and Interconnect Using Ink–Jet Printing Technology", Hayes, D. et al., Display Works '99, MicroFab Technologies, Inc., pp. 1–4, 1999.

"Ink–Jet Based Fluid Microdispensing in Biochemical Applications", Wallace, D., MicroFab Tecnologies, Inc., Laboratory Automation News, vol. 1, No. 5, pp. 6–9, Nov., 1996.

"Protorealistic Ink–Jet Printing Through Dynamic Spot Size Control", Wallace, D., Journal of Imaging Science and Technology, vol. 40, No. 5, pp. 390–395, Sep./Oct. 1996.

"MicroJet Printing of Solder and Polymers for Multi–Chip Modules and Chip–Scale Package", Hayes, D., et al., MicroFab Technologies, Inc.

"A Method of Characterisstics Model of a Drop–on–Demand Ink–Jet Device Using an Integral Method Drop Formation Model", Wallace, D., MicroFab Technologies, Inc., The American Society of Mechanical Engineers, Winter Annual Meeting, pp. 1–9, Dec. 10–15, 1989.

"Digital Imaging Equipment White Papers", Putting Damaged Film on ICE, www.nikonusa.com/reference/whitepapers/imaging, Nikon Corporation, Nov. 28, 2000.

* cited by examiner

METHOD AND APPARATUS TO PRE-SCAN AND PRE-TREAT FILM FOR IMPROVED DIGITAL FILM PROCESSING HANDLING

This application claims the benefit of U.S. Provisional Application No. 60/173,648, filed Dec. 30, 1999, the entire disclosure of which is hereby incorporated herein by reference.

TECHNICAL FIELD

The present invention relates generally to the field of digital film processing, and more particularly, to an apparatus and method for pre-screening and pre-treating film that is amenable to digital film processing.

BACKGROUND OF THE INVENTION

Standard color photographic negative film that is widely used in still cameras today is designed and manufactured to contain three superimposed, semi-independent color sensing layers. Spectral sensitivity curves for photographic negative film show the typical response of the three layers of photographic film over the visible light spectrum; assuming equal radiated power at each wavelength. In particular, it is known that the top layer responds primarily to light of short wavelength (blue light), the middle layer responds primarily to light of medium wavelength (green light) and the bottom layer responds to light of long wavelength (red light). When film with these types of spectral sensitivities is exposed to visible light, each spot on the film records the amount of blue, green and red light, or flux. Incident flux creates what is referred to as the latent image.

In conventional color photographic development systems, the exposed film is chemically processed to produce dyes in the three layers with color densities directly proportional to the blue, green, and red spectral exposures that were recorded in the latent image. Yellow dye is produced in the top layer, magenta dye in the middle layer, and cyan dye in the bottom layer. Through a separate conventional process, positive photographic images may then be electronically scanned to produce a digital image.

Conventional electronic scanning of developed photographic negative film to produce digital images is done by passing visible light through the developed negative and using filters with appropriate spectral responsivities to detect, at each location on the film, the densities of the yellow, magenta and cyan dyes in the photographic negative. The density values detected in this way are indirect measures of the blue, green and red light that initially exposed each location on the film. These measured density values constitute three values used as the blue, green and red values for each corresponding location, or pixel, in the digital image. Further processing of these pixel values is often performed to produce a digital image that accurately reproduces the original scene and that is pleasing to the human eye.

Image enhancement has been the subject of a large body of film processing technology. A common feature of all digital film processing technology is that the film to be scanned must be relatively flat during the optical scan. Furthermore, the optical scan best occurs using a relatively uniform velocity during the scan period. Small imperfections in the film, such as tearing, creases, scratches, foreign objects and fluids decrease the efficacy of the digital scan. Large imperfections make digital film processing and conventional scanning very difficult.

Large imperfections to the film surface, such as broken, ripped or torn sprocket holes, are encountered frequently during automated film processing. In film processing using chemical development tanks, tears to the sprocket holes are generally not an issue because they are not used to transfer the film from tank to tank. For example, torn sprocket holes occur when the user, or in the case of automated cameras, the auto-drive advances the film too far, breaking one or more of the sprocket holes.

In addition to large imperfections, such as sprocket hole breakage, other imperfections may occur when foreign objects, such as water, particles (e.g., dust), and oils contact the film. Exposure to these foreign objects may even occur while the film is still in its original canister. Creases in the film are yet another imperfection that may occur when the film is reverse-wound.

SUMMARY OF THE INVENTION

The present invention relates to pre-screening and/or pre-treating film before further chemical processing and scanning. Presently, conventional systems do not take into consideration of the special needs of digital film processing ("DFP") techniques and devices. The present invention can correct, to the extent possible, film imperfections prior to processing. In at least one embodiment, imperfections in the film can be identified and then corrected.

In a particular embodiment, the present invention comprises an apparatus for use in digital image processing in which the suitability of a film for DFP is determined prior to scanning. The apparatus for use with the invention includes, generally, a sensor for detecting one or more imperfections on the film and a microprocessor connected to the sensor that determines the amount and extent of imperfections of the film based on one or more reference readings. A reference sensor and a memory may be connected to the microprocessor to provide the reference readings. The reference sensor readings may be determined by the reference sensor and stored in the memory for use by the microprocessor. The reference sensor may be a reflective sensor or a sensor that reads light that traverses the film, is reflected by the film or both.

In a particular embodiment of the invention, the apparatus may also include a tape dispenser positioned to repair the film if the imperfection detected by the sensor is a breakage in the film. For example, the sensor may detect abnormalities in the shape of the perforations or sprockets on the film. Another imperfection that may be detected, and in some embodiments corrected, is the detection of moisture on the film (or even the actual moisture level). If excessive moisture is detected, as determined in the comparison of actual and reference measurements, the film is dried until the moisture level drops below the predetermined acceptable moisture level. Film may be dried using, for example, a blower, a vacuum or even rollers that remove moisture mechanically or by capillary action.

When the sensor detects foreign objects on the film, these may be removed using a variety of systems. One such system is the use of a blower, a vacuum or both to remove the foreign object. Another system may use one or more rollers that mechanically remove the foreign object, e.g., tacky rollers. When the sensor detects one or more foreign objects on the film, the microprocessor compares the amount of foreign object(s) on the film to reference levels, and if the level is above a predetermined acceptable foreign object level, the film is cleaned until the foreign object level drops below the predetermined acceptable foreign object level.

Yet another embodiment of the present invention is a method of identifying film suitable for digital image processing that includes the steps of: exposing film to one or more light sources; detecting the light reflected from the film to measure imperfections on the film; determining if the imperfections on the film exceed reference sensor readings; and routing the film based on the sensor output depending on whether the film is suitable for digital film processing from film that is not suitable for digital film processing. The method may also include the steps of: determining the level of moisture in the film, detecting foreign objects on the film; and scanning for one or more broken sprockets on the film edges. Imperfections in the moisture level, the presence of foreign objects and broken sprockets will lead to rejection of the film from further digital film processing. The invention may also include one or more of the following film imperfection correction systems. Imperfections on the film are corrected selecting a remedial measure that corrects the imperfection, for example, where excessive moisture and foreign objects are detected they are removed. Likewise, if one or more broken sprockets are detected, they may be repaired using, e.g., a tape dispenser mechanism prior to digital film processing.

Other embodiments of the present invention may include always cleaning the film and then inspecting the film, or performing the cleaning and inspection steps in an iterative manner. The results of the inspection may then be reported to an operator or recorded in some manner. If the film is rejected, it can be rolled back into the canister or stored in a new canister or storage device. Moreover, the present invention may report the specific reasons why the film was rejected and identify where on the film the problems were detected.

To clean the film upon detection of imperfections, or as a standard procedure, a particle removal member can be utilized. In one embodiment, the particle removal member which can be easily and efficiently cleaned when a need for cleaning is identified. In particular, the particle removal member can be periodically cleaned by a cleaning system which is adapted for removing particles from the particle removal member. In this embodiment, the cleaning system and the particle removal member are relatively movable so as to be selectively contactable with respect to each other. The cleaning system has a particle adhering surface which is operative to remove particles from the particle removal member when the cleaning system is in contact with the particle removal member. The particle adhering surface can comprise disposable adhesive tape and a tape transport system can be used to advance the tape across a cleaning member, such as a roller for example. The cleaning system can automatically move into contact with the particle removal member at predetermined times, such as detection of a passage of time or an amount of usage for example. Other features and advantages of the present invention shall be apparent to those of ordinary skill in the art upon reference to the following detailed description taken in conjunction with the accompanying drawings.

BRIEF DESCRIPTION OF THE DRAWINGS

The above and further advantages of the invention may be better understood by referring to the following description in conjunction with the accompanying drawings in which corresponding numerals in the different figures refer to corresponding parts in which.

DETAILED DESCRIPTION OF EXEMPLARY EMBODIMENTS

While the making and using of various embodiments of the present invention are discussed herein in terms of a digital film processing system, it should be appreciated that the present invention provides many applicable inventive concepts which can be embodied in a wide variety of specific contexts. For example, the present invention can be used to pre-scan and pre-treat any strip of material. The specific embodiments discussed herein are merely illustrative of specific ways to make and use the invention and do not delimit the scope of the invention.

The term "film" is used hereinafter to refer to any unrestricted length of material. The film may or may not have aligned and evenly spaced perforations, which are hereinafter referred to as "sprocket holes." Camera or motion picture film is, of course, a primary example, but the present invention is not to be construed to be limited to a film for still camera or even motion picture film. The film may be a strip of material for other purposes as well.

Figure 1:
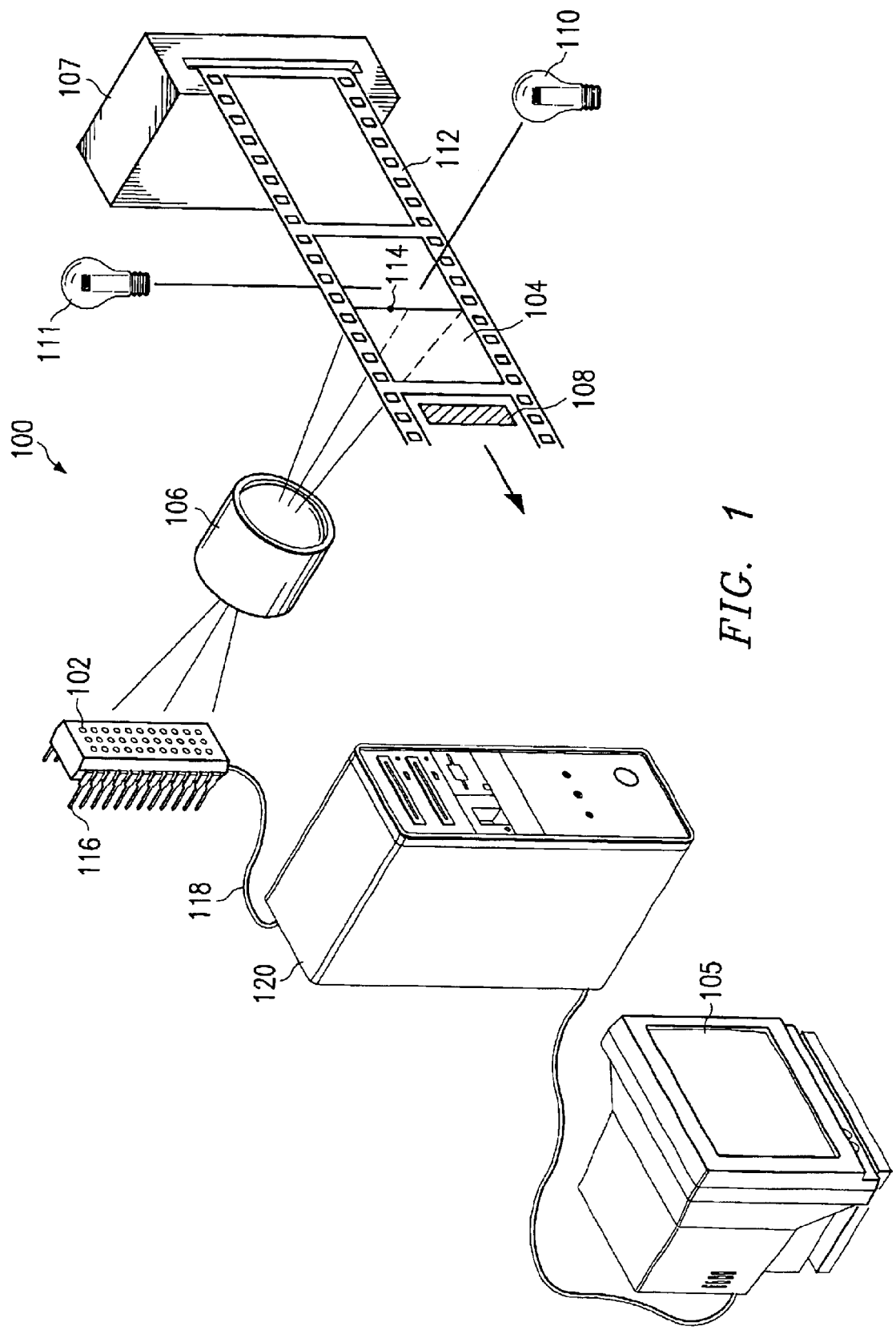
FIG. 1 is a perspective view of a scanning device in accordance with the present invention.

An improved digital film scanning apparatus is shown in FIG. 1. The scanning apparatus 100 operates by converting electromagnetic radiation from an image to an electronic (digital) representation of the image. The image being scanned is typically embodied in a physical form, such as on a photographic media, i.e., film, although other media may be used. In general, the electromagnetic radiation used to convert the image into a digitized representation is preferably infrared light. The scanning apparatus 100 generally includes a number of optic sensors 102. The optic sensors 102 measure the intensity of electromagnetic energy passing through or reflected by the film 112. The source of electromagnetic energy is typically a light source 110 which illuminated the film 112 containing the scene image 104. Radiation from the source 110 may be diffused or directed by additional optics such as filters (not shown) and one or more lenses 106 positioned near the sensors 102 and the film 112 in order to illuminate the images 104 and 108 more uniformly. Furthermore, more than one source may be used. Source 110 is positioned on the side of the film 112 opposite the optic sensors 102. This placement results in sensors 102 detecting radiation emitted from source 110 as it passes through the image 104 on the film 112. Another radiation source 111 is shown placed on the same side of the film 112 as the sensors 102. When source 111 is activated, sensors 102 detect radiation reflected by the images 104 and 108. This process of using two sources positioned on opposite sides of the film being scanned is described in more detail below in conjunction with FIG. 2.

The optic sensors 102 are generally geometrically positioned in arrays such that the electromagnetic energy string each optical sensor 102 corresponds to a distinct location 114 in the images 104 and 108. Accordingly, each distinct location 114 in the scene image 104 corresponds to a distinct location, referred to as a picture element, or pixel for short, in the scanned, or digitized image. The image 104 on film 112 is usually sequentially moved, or scanned, across the optical sensor array 102. The optical sensors 102 are typically housed in a circuit package 116 that is electrically connected, such as by cable 118, to supporting electronics for computer data storage and processing, shown together as computer 120. Computer 120 may then process the digitized image 105. Alternatively, computer 120 may be replaced with a microprocessor and cable 118 replaced with an electrical circuit connection.

Optical sensors 102 may be manufactured from different materials and by different processes to detect electromagnetic radiation in varying parts and bandwidths of the electromagnetic spectrum. The optical sensor 102 may include a photodetector (not expressly shown) that produces an electrical signal proportional to the intensity of electromagnetic energy striking the photodetector. Accordingly, the photodetector measures the intensity of electromagnetic radiation attenuated by the image 104 on film 112.

Figure 2:
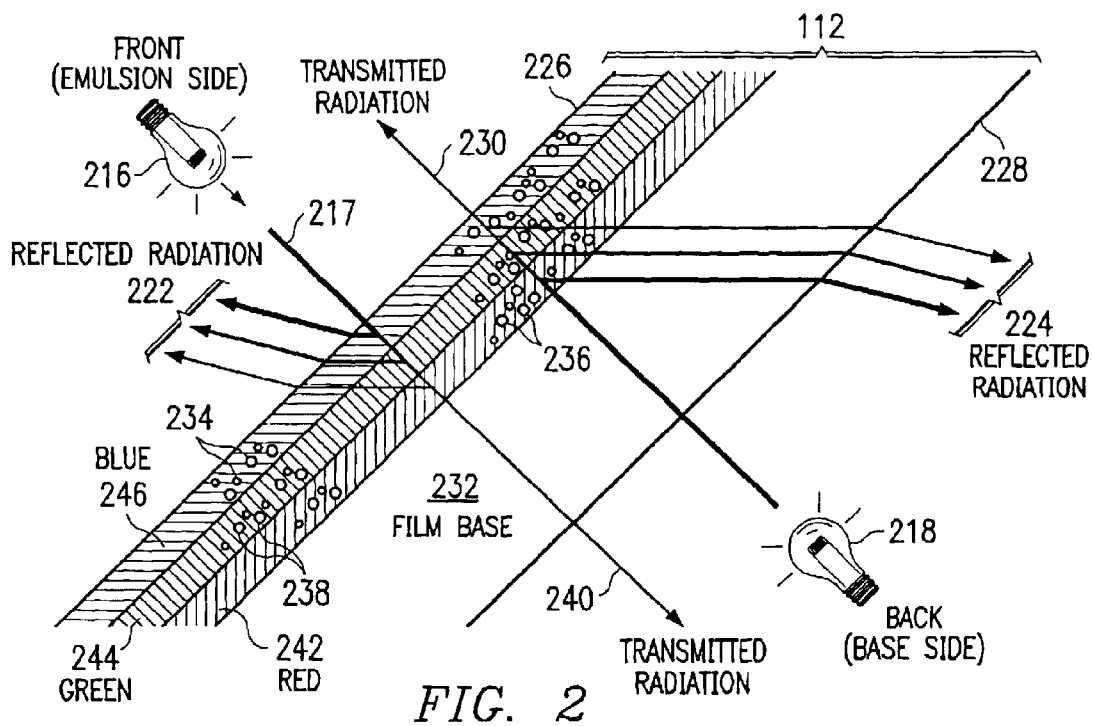
FIG. 2 is an illustration of a digital film processing system which uses duplex film scanning in accordance with the present invention.

Turning now to FIG. 2, a conventional color film 112 is depicted. As previously described, the present invention uses duplex film scanning that refers to using a front source 216 and aback source 218 to scan the film 112 with reflected radiation 222 from the front 226 and reflected radiation 224 from the back 228 of the film 112 and by transmitted radiation 230 and 240 that passes through all layers of the film 112. While the sources 216, 218 are generally monochromatic and preferably infrared. The respective scans, referred to herein as front, back, front-through and back-through, are further described below.

In FIG. 2, separate color levels are viewable within the film 112 during development of the red layer 242, green layer 244 and blue layer 246. Over a clear film base 232 are three layers 242, 244, 246 sensitive separately to red, green and blue light, respectively. These layers are not physically the colors; rather, they are sensitive to these colors. In conventional color film development, the blue sensitive layer 246 would eventually develop a yellow dye, the green sensitive layer 244 a magenta dye, and the red sensitive layer 242 a cyan dye.

During film development, layers 242, 244, and 246 are opalescent. Dark silver grains 234 developing in the top layer 246, the blue source layer, are visible from the front 226 of the film, and slightly visible from the back 228 because of the bulk of the opalescent emulsion. Similarly, grains 236 in the bottom layer 242, the red sensitive layer, are visible from the back 228 by reflected radiation 224, but are much less visible from the front 226. Grains 238 in the middle layer 244, the green sensitive layer, are only slightly visible to reflected radiation 222, 224 from the front 226 or the back 228. However, they are visible along with those in the other layers by transmitted radiation 230 and 240. By sensing radiation reflected from the front 226 and the back 228 as well as radiation transmitted through the developing film 112 from both the front 226 and back 228 of the film 112, each pixel for the film 112 yields four measured values, one from each scan, that may be mathematically processed in a variety of ways to produce the initial three colors, red, green and blue, closest to the original scene.

The front signal records the radiation 222 reflected from the illumination source 216 in front of the film 112. The set of front signals for an image is called the front channel. The front channel principally, but not entirely, records the attenuation in the radiation from the source 216 due to the silver metal particles 234 in the top-most layer 246, which is the blue recording layer. There is also some attenuation of the front channel due to silver metal particles 236, 238 in the red and green layers 242, 244.

The back signal records the radiation 224 reflected from the illumination source 218 in back of the film 112. The set of back signals for an image is called the back channel. The back channel principally, but not entirely, records the attenuation in the radiation from the source 218 due to the silver metal particles 236 in the bottom-most layer 242, which is the red recording layer. Additionally, there is some attenuation of the back channel due to silver metal particles 234, 238 in the blue and green layers 246, 244.

The front-through signal records the radiation 230 that is transmitted through the film 112 from the illumination source 218 in back of the film 112. The set of front-through signals for an image is called the front-through channel. Likewise, the back-through signal records the radiation 240 that is transmitted through the film 112 from the source 216 in front of the film 112. The set of back-through signals for an image is called the back-through channel. Both through channels record essentially the same image information since they both record the attenuation of the radiation 230, 240 due 110 to the silver metal particles 234, 236, 238 in all three red, green, and blue recording layers 242, 244, 246 of the film 112.

Several image processing steps are then used to convert the illumination source radiation information for each channel to the red, green, and blue values similar to those produced by conventional scanners for each spot on the film 12. These steps are used because the silver metal particles 234, 236, 238 that form during the development process are not spectrally unique in each of the film layers 242, 244, 246. These image processing steps are not performed when conventional scanners are used because the dyes which are formed with conventional chemical color processing scanners, once initial red, green and blue values are derived for each image, further processing of the red, green and blue values is usually done to produce images that more accurately reproduce the original scene and that are pleasing to the human eye.

Because the scanning described above occurs during film development rather than after the film is developed, the digital film processing system shown in FIGS. 1 and 2 can produce multiple digital image files for the same frame at different film development times, each image file having back, front, and through values which are created using the duplex scanning method described above. It may be desirable to create multiple duplexscanned image files for the same frame at separate development times so that features of the image which appear at various development times can be recorded. During the film development process, the highlight areas of the image (i.e., areas of the film which were exposed to the greatest intensity of light) will develop before those areas of the film which were exposed to a lower intensity of light (such as areas of the film corresponding to shadows in the original scene). Thus, a longer development time will allow shadows and other areas of the film which were exposed to a low intensity of light to be more fully developed, thereby providing more detail in these areas. However, a longer development time will also reduce details and other features of the highlight areas of the image. Thus, in conventional film development, one development time must be selected and this development time is typically chosen as a compromise between highlight details, shadow details and other features of the image which are dependent on the duration of development. Scanning this developed film image using a conventional film scanner will not revive any of these details which are developmenttime dependent. However, in the digital film processing system of FIGS. 1 and 2, such a compromise need not be made, as digital image files for the same image can be created at multiple development times while the film develops, and these multiple images can be combined to produce an enhanced image.

Figure 3:
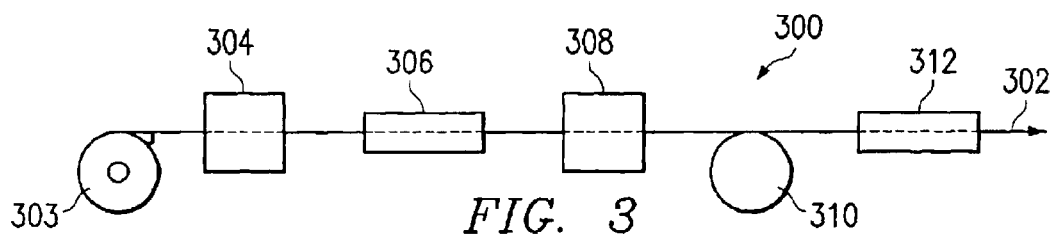
FIG. 3 shows a configuration of a film pre-scan apparatus in accordance with the present invention.

In FIG. 3 a configuration of a film pre-scan apparatus 300 is shown in accordance with the present invention. Prior to opening a film canister 303, it may be inspected to ensure that it is, or has been generally kept, in good condition, e.g., that the canister 303 is dry and does not exhibit structural damage. Upon approval for further processing, the film 302 within the canister 303 is then removed. Removal of the film 302 from the canister 303 may be accomplished by opening the canister 303 mechanically or by capturing the film 302 and pulling it out of the canister 303. Often, removal of the film 302 leads to destruction of the canister 303 using, e.g., a shred technique or punch technique. Alternatively, the film 302 is pulled from within the canister 303 by sliding a capturing extension into the canister 303 and pulling the film 302 out by the film tongue. The film 302 may or may not be cut away from the spool prior to further processing.

Once the film 302 is pulled out of its canister 303, a scanner 304 detects for any imperfections, such as moisture, oil, foreign objects, particles, creases, tears, or broken sprocket holes, in the film 302. The film 302 is scanned or inspected for imperfections in a totally light tight enclosure using an infrared or near infrared light source and a scanner 304. The scanner 304 may be connected to a microprocessor and a memory that stores reference data for comparison to the actual data measured by the scanner 304. The scanner 304 may be, e.g., a reflective scanner, wherein transmitted light, e.g., infrared or near infrared light, strikes the film 302 and is reflected back to a sensor. The reflected light is then measured and the difference in reflectivity is used to determine if the film 302 is damaged or contains imperfections. A reference sensor and a memory may be connected to the microprocessor to provide the reference readings or data. The reference sensor readings may be determined by the reference sensor and stored in the memory for use by the microprocessor. The reference sensor may be a reflective sensor or a sensor that reads light that is transmitted through the film, is reflected by the film or both. Alternatively or concurrently, light that is transmitted through the film 302 may be detected and used to measure potential film imperfections. Upon verification that there is nothing wrong with the film 302 and that the film 302 is suitable for DFP processing, the film 302 may then be cut, rolled onto a spool and put into a DFP system or other processing system.

If imperfections are detected, however, a series of remedial steps may be taken prior to determining that the film is unsuitable for DFP and should be routed for regular chemical processing and development. It is important to make a determination of suitability for DFP prior to initiating DFP because deposition of the thin chemical film layer in DFP irreversibly renders the film unsuitable for regular chemical bath or tank film processing.

A vacuum/blower 306 may be used to remove foreign objects and even moisture from the film 302. Alternatively, the film 302 may be rewound back into the canister 303 and the reasons for the rejection of the film 302 may be reported to the operator of the pre-scan apparatus 300. A tape dispenser 308 is also shown in the path of the film 302 in which any damaged sprockets may be repaired. Take-up spool 310 is positioned in-line with the film 302 to provide for a place where repaired and cleaned film 302 is stored prior to DFP. Alternatively, take-up spool 310 may be used to gather film 302 that will not be eligible for DFP, in which case the rejected film is once again placed in a light-tight container for transport to standard chemical processing. Alternatively, the film 302 is taken from the take-up spool 310 and cut in cutter 312 for capture by the rollers that will feed the film 302 into a DFP system.

The pre-scan apparatus 300 may incorporate other remedial measures to prepare the film 302 for processing. In the case of water-based imperfections, e.g., when the film 302 has been exposed to water inside the canister 303 when dropped into water or exposed to a high moisture atmosphere, moisture content may be determined using a hydrometer. Alternatively, moisture may be detected by noting increased specular reflections from the emulsion side of the film 302 relative to the nominal reflection expected for dry film. Depending on the moisture reading, the film 302 may then be routed into an air-based dryer or passed through rollers that remove water. The film 302 may then be certified for DFP and routed into a DFP apparatus.

Another type of imperfection that may be detected is dust and other foreign objects on the surface of the film 302. A number of debris removal systems may be used to remove foreign objects from the film 302. For example, foreign objects may be removed by running the film through tacky rollers that mechanically remove foreign objects by having a higher adherence to the foreign object than the film emulsion. The rollers may be replaced or cleaned once a sufficient amount of foreign objects are collected on the rollers. An embodiment of a cleaning system for such rollers is discussed in more detail below. Foreign objects may also be removed by a vacuum, a blower or both 306, wherein the foreign objects are sucked or blown off the film 302. The blower/vacuum method will be useful for the removal of dust that collects on the film during storage or upon exposure to dusty conditions as well as removal of damaged film sprocket debris. After cleaning, the film 302 is scanned again to determine if the film has been cleaned sufficiently for DFP. Upon certification for DFP the film 302 may be routed into a DFP apparatus.

Another imperfection is the breaking of sprocket holes or perforations. In ordinary use, the perforations along film 302, such as still camera picture film, are engaged by drive sprockets or a shuttle arm used to feed the film into a camera or other device. As the film 302 is advanced, the film 302 often tears around the perforations, particularly at the beginning and end of a roll of film 302. In those, and other cases of damage to the perforations, it may be desirable to repair the film 302 by bonding a strip of pre-perforated or unperforated tape along the film 302 where damage has occurred, with the perforations of the tape aligned with the sprocket holes of the film 302.

Apparatus and methods for attaching pre-perforated or even non-perforated tape to film 302 are known in the art and may be used to repair the film 302 prior to DFP. One example of such a system is disclosed in U.S. Pat. No. 3,959,048 in which: an arrangement for bonding preperforated repair tape to motion picture film with the precision required to align the tape perforations with the film perforations along the length of the tape, is disclosed. Improvements over that arrangement are disclosed in U.S. Pat. No. 4,026,756, in which the problem of aligning the perforations of the repair tape with the perforations of the film along the length of the film is shown. By adding or repairing the film 302 with tape, whether perforated or not, the potential for problems in the DFP system is decreased.

Other improvements to sprocket repair techniques come from the transverse alignment of the repair tape to maintain side edges of holes in the repair tape in line with side edges of holes in the film 302, and more particularly to assure firm bonding of the repair tape on the film 302 along side edges of holes and between holes. U.S. Pat. No. 4,249,985 issued to Stanfield uses a pressure roller having "apertures" or recesses shaped and spaced to receive sprockets on the sprocket wheel, thereby to apply pressure to the adhesive tape all around a sprocket hole. Initial adjustment of the roller during the start of each repair run may be used to assure that the sprockets are aligned with roller apertures. Alternatively, the pressure roller in the second roller may be grooved. Using a grooved roller has the advantage that the repair tape between sprocket holes is applied around each sprocket hole. A sprocket wheel at the repair station may be used to pull repair tape from a roll on a spindle for bonding onto perforated film fed directly from a supply reel through a guide to the sprocket wheel. A sponge rubber pressure roller on a spring loaded lever may be used to press the film onto the repair tape for pressure bonding.

The term "sponge rubber" is used herein, in a generic sense to refer to resilient, porous (closed cell) material used for the roller or may even be a soft rubber roller. Another example of a suitable material that may be used is a nitrite rubber that is commercially available, but any other nitrite rubber (a class of synthetic rubbers) may be used. All that is required is that the resilient material used be formed with closed cells to resemble a sponge, with sufficient density to permit the material, cut or formed into the shape of a roller, to function as a pressure roller while allowing the sprockets to penetrate into the material.

Figure 4:
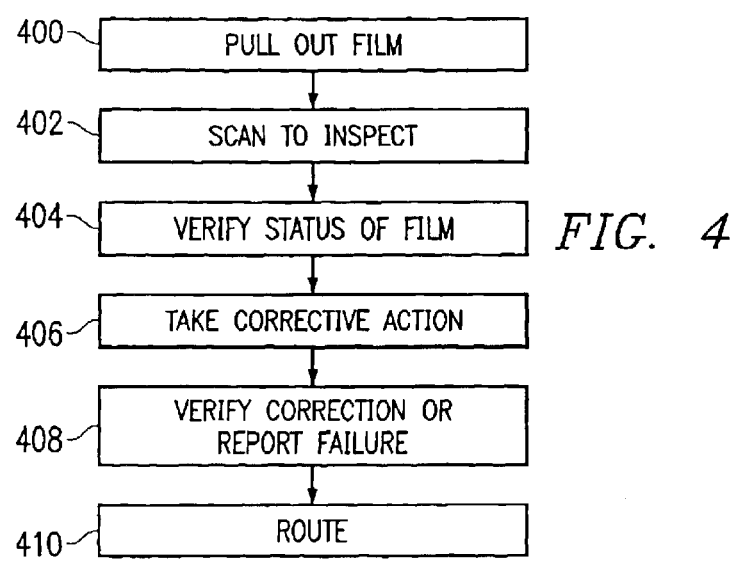
FIG. 4 is a flow chart of a method for pre-scanning film in accordance with the present invention.

FIG. 4 is a flow chart of a method for pre-scanning film in accordance with the present invention. At block 400, the film is removed from its container and spooled into the pre-scan system. The film may be cut at this stage, however, it is envisioned that if film is to be rejected it would best be kept at its full length. At block 402, the film may be inspected visually by a user under infrared or near infrared light during the pre-scan using the one or more sensors of the present invention. At block 404, the status of the film is verified, that is, a determination is made whether remedial measures should be taken to bring the film into compliance with the DFP system requirements as compared to reference levels. Alternatively, the film may be rewound back into the canister and the reasons for the rejection of the film may be reported to the pre-scan apparatus operator. At block 406, the problem or problems, if any, are categorized and remedial measures are taken.

Examples of remedial measures include the use of vacuum/blower or tacky rollers to clean liquid and solid foreign object impurities from the film. Alternatively, the problem may be with broken, scratched, backward or bent film. If the sprockets are broken, for example, the film is directed into a tape dispenser that corrects for the loss of lateral support in the film for the images that are captured on the film. The lateral support for the images is most often necessary for the DFP process because of the need to maintain the film as flat as possible. The determination is made, at block 408, whether the film has been repaired and if the remedial measures are sufficient for further processing or if the film must still be rejected. At block 410, the film is routed into the DFP system for further processing or the film is rejected from DFP and directed toward a regular chemical bath processing system. This may involve rewinding the film into the original canister or transferring the film to a holding location for manual removal.

Other embodiments of the present invention may include always cleaning the film and then inspecting the film, or performing the cleaning and inspection steps in an iterative manner. The results of the inspection may then be reported to an operator or recorded in some manner. If the film is rejected, it can be rolled back into the canister or stored in a new canister or storage device. Moreover, the present invention may report the specific reasons why the film was rejected and identify where on the film the problems were detected.

Figure 5:
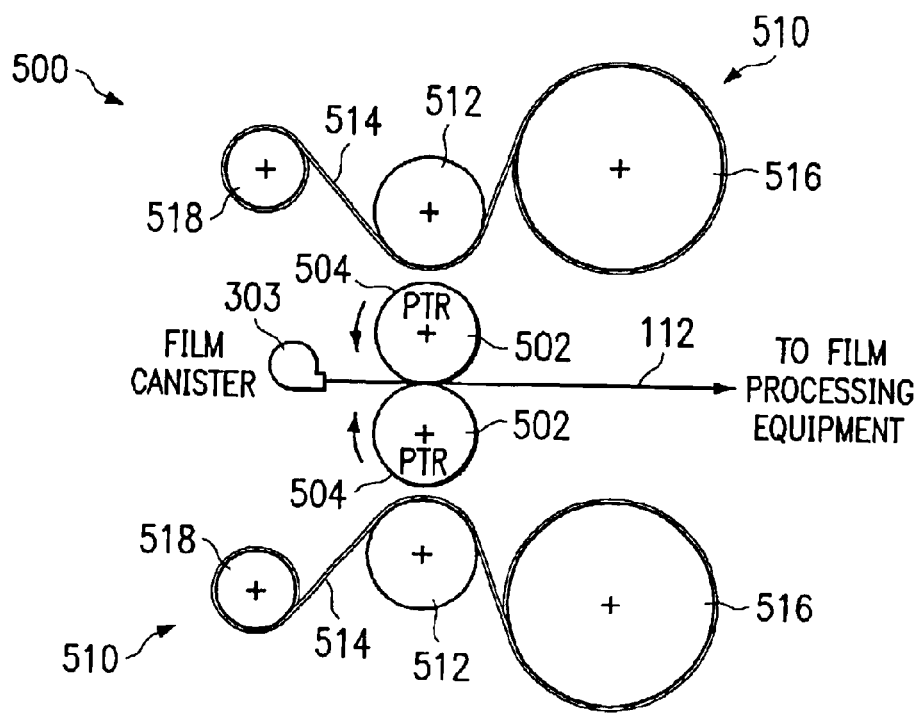
FIG. 5 is a schematic diagram of film cleansing system which can be used to efficiently clean film prior to digital film processing.

FIG. 5 is a schematic diagram of film cleansing system 500 which can be used to efficiently clean film prior to digital film processing. Generally, the system includes a particle removal member 502 which removes particles from the film 112, and a cleaning system 510 which selectively cleans particles from the particle removal member 502 as needed.

More specifically, in this exemplary embodiment, a pair of particle removal members 502 are provided to remove particles, such as dust, lint, hair, particulate, and the like, from opposing surfaces of the film 112. In this example, the particle removal members 502 comprise particle take-off (i.e., removal) rollers, and the film is fed between the two rollers 502. To feed the film 112 from the film canister 303 and through these rollers 502, any suitable film transportation system can be utilized, such as those which comprise nip rollers, sprockets, motors, belts, guides, conveyors, and the like, and which contact the film in order to transport the film in a predetermined path. As the film 112 makes contact with the particle removal rollers 502 and moves therebetween, particles are transferred from the film to the rollers 502. This can occur by providing the rollers 502 with a particle attraction surface 504 which removes the particles from the film 112. This surface 504 can comprise a tacky or adhesive surface to which the particles adhere as the roller 502 contacts the film 112. However, any suitable particle attraction surface 504 may be utilized, such as those which attract particles through electric charge, suction force, magnetism, or any other suitable force.

As can be understood, the particle removal members 502 will need periodic cleaning as film is moved therethrough and particles build thereon. Accordingly, a cleaning system 510 can be used to selectively clean each removal member 502 when needed or desired. In this exemplary embodiment, each cleaning system 510 includes a cleaning member 512 for a particle removal member 502. Each cleaning member 512 is relatively movable with respect to its corresponding particle removal member 502 such that it can move into and out of contact with the particle removal member, to selectively remove particles from the particle removal member. In this example, the cleaning member 512 comprises a contact roller which can be moved or indexed between a non-contacting position (shown in FIG. 5) and a contacting position (shown in FIG. 6). When in the contacting position of FIG. 6, the contact roller 512 removes particles from the particle removal roller 502 and thereby cleans that roller. Accordingly, in the contacting position of FIG. 6, as the roller 502 rotates, the contact roller 512 also rotates and the contact between the removal roller 502 and the contact roller 512 (which can include a material over the roller) causes particles to be transferred from the removal roller to the contact roller, such that the removal roller is cleaned.

Figure 6:
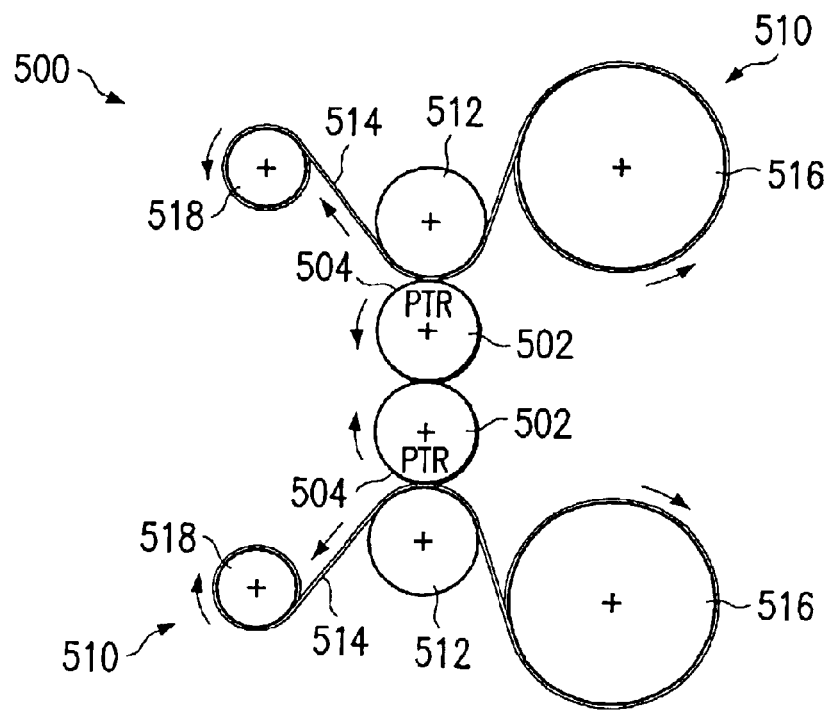
FIG. 6 is schematic diagram of the system of FIG. 5, illustrating a cleaning member in the contacting position for removal of particles from the particle removal member.

An adhesive or attractive force can be utilized to cause a contact roller 512 to attract particles from a particle removal roller 502, when in the contacting position of FIG. 6. For example, in the exemplary embodiment of FIGS. 5 and 6, an adhesive tape 514 is fed over the contact roller 512 and used to attract the particles from the particle removal roller 502. Accordingly, when a roller 512 is brought in contact with a particle removal roller 502 for performing the cleaning process, the tape 514 is fed between the rollers 502 and 512 and attracts many of the particles which were removed from the film by the roller 502. In this way, the roller 502 is cleaned when needed or desired.

To move the tape 514 over the contact roller 512, any of a variety of suitable tape transport systems can be utilized. In this embodiment, the tape is supplied via a supply roll 516 and is wound onto a take-up roller 518. To transport the tape 514 from the supply roll 516 to the take-up roller 518, a motor or other suitable actuator can: be utilized. For example, the tape could be initially threaded from the supply roll 516 over the contact roller 512 and to the take-up roller 518, and the take-up roller can be rotated by a motor, such as a DC motor, a stepper motor, or any other suitable motor. However, other appropriate actuators, conveyors, rollers, and the like can be utilized to transport the tape 514.

FIG. 5 illustrates the non-contacting position of each cleaning system 510. In this position, the particle removal rollers 502 remove particles from the opposing sides of the film 112 by contact with the film. The film 112 then moves to the film processing equipment, such as the duplex scanning equipment described above for example, after being cleaned by the particle removal rollers 502. However, particles build up on the rollers 502 and it is desirable to easily clean these rollers 502 when needed or desired.

Accordingly, when cleaning of a roller 502 is desired, a contact roller 512 is moved to the contacting position shown in FIG. 6. This may occur when no film is being moved through the system 500 or when film is being moved through the system. In this exemplary embodiment, the contact roller 512 is movable along a path, such as via a guide, between the two positions shown in FIGS. 5 and 6. During cleaning of the roller 502, the tape 514 is moved from its corresponding supply roll 516 to its take-up roller 518 and passes over its corresponding contact roller 512. Accordingly, when a cleaning system 510 is in the contacting position, the tape 514 of that system is positioned between the contact roller 512 and the particle removal roller 502, and is in contact with both of these rollers 502 and 512. The tape 514 is wound about the take-up roller 518 as the cleaning takes place. As the tape 514 moves past particle take-up roller 502, it collects particles from that roller, and thereby cleans the roller. The tape 514 may be moved a predetermined distance, for a predetermined time, or for a predetermined number of revolutions of one of the rollers. As shown, two cleaning systems 510 can be provided to clean both particle removal members 502 (if multiple members 502 are utilized).

Once the cleaning is complete, the movement of the tape 514 is stopped, and the contact roller 512 is returned to the non-contacting position of FIG. 5. Periodic cleanings can occur until all tape 514 has been transferred from the supply roll 516 to the take-up roller 518. At this time, the tape 514 on the roller 518 can be simply discarded, and a new supply roll 516 provided, such that new tape 514 can be threaded over the contact roller 512 to the take-up roller 518.

Cleanings can be initiated by the user by moving the contact roller 512 to the position of FIG. 6 and beginning to wind the tape 514 about the take-up roller 518. These movements can be initiated under the power of motors or other actuators, such as discussed above. These movements can also be initiated automatically. For example, a controller can initiate the movements at predetermined times. In particular, the controller can sense when the particle removal roller 502 has completed a given number of revolutions, and can then initiate the movements of the cleaning system 510 to clean the roller 502. Alternatively, the controller can sense the time that the film cleansing system 500 has been in operation since the last cleaning of the rollers 502, or the number of film rolls cleaned since the last cleaning of the rollers 502, and, upon reaching a predetermined maximum value, initiate the movements one or more of the cleaning systems 510 to clean the rollers 502.

Figure 7:
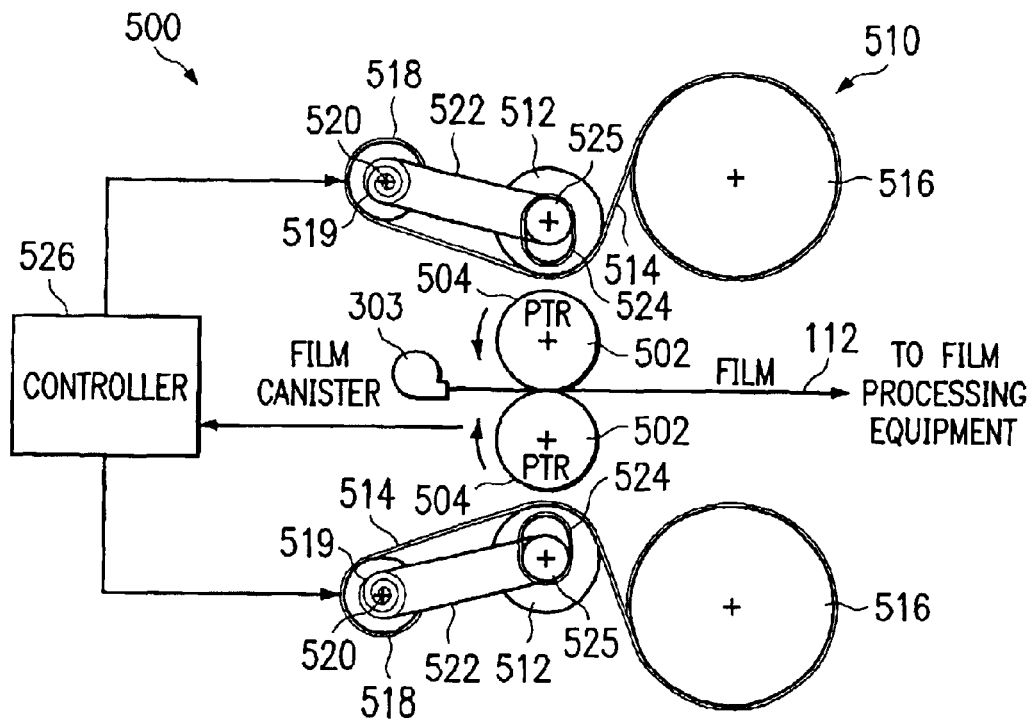
FIGS. 7 and 8 are schematic diagrams showing an indexing system for automatic movement of the cleaning member of FIG. 6 between a contacting and a non-contacting position.
Figure 8:
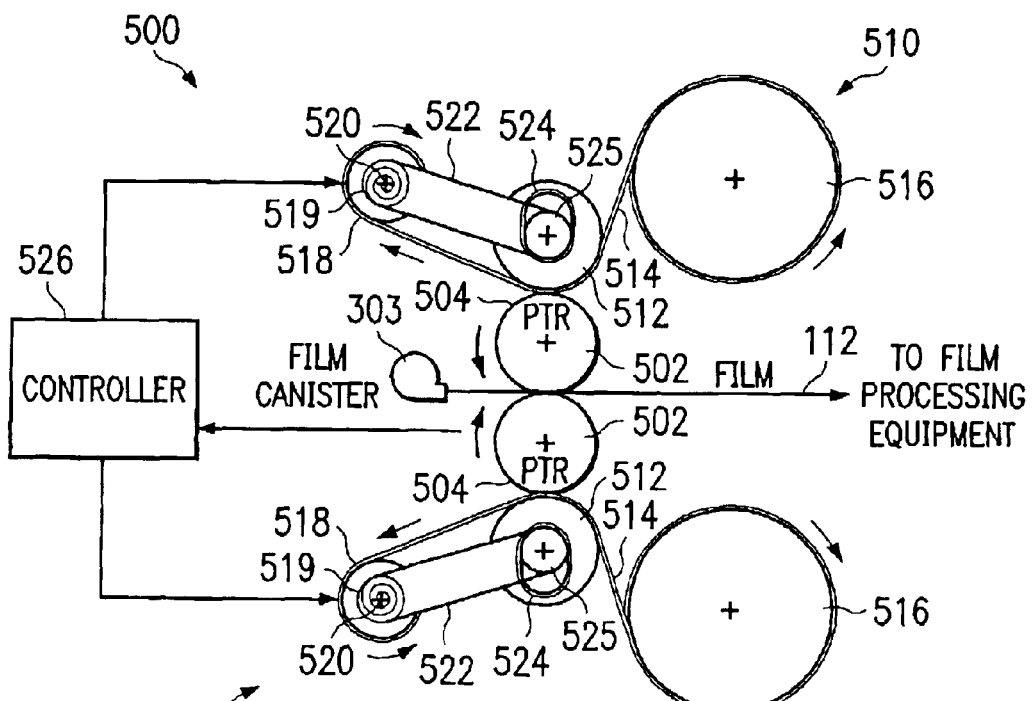

FIGS. 7 and 8 illustrate one exemplary system for use in moving the contact roller 512 from the non-contacting position to the contacting position. In this example, the contact roller 512 is connected to a shaft 525 which is slidingly movable within a guide 524. The shaft 525 of that contact roller 512 is connected to the shaft 519 of the take-up roller 518 via a link 522, such as a chain or belt for example. A biasing member 520, such as a clock spring or spiral spring for example, provides a force which keeps the contact roller 512 in the non-contacting position when not in use. When cleaning of a particle removal member 502 is to commence, however, the motor or actuator connected to the shaft 519 of the take-up roller 518 is activated and causes the shaft 519 and roller 518 to rotate. This rotation is transmitted via the linkage 522 to cause simultaneous rotation of the shaft 525 and contact roller 512. The torque produced by this rotation lowers the contact roller 512 to the contacting position shown in FIG. 8. The rotation also causes the tape 514 to move from the supply roll 516, over the contact roller 512, and to the take-up roller 518. During this movement of the tape 514, contact of the tape 514 with the particle removal roller 502 cleans the roller 502. The motor which produces the motion of the rollers and the tape can be any of a variety of suitable motor, such as DC motors or stepper motors for example, and motion of the rollers can be accomplished via suitable linkages, gears, shafts, and related devices. A slip clutch can be provided to prevent torque overload of the contact roller 512 against the particle removal roller 502. The clutch can be sized and configured to slip once a predetermined maximum torque is reached (e.g., one pound-inch), in order to keep the load constant.

As also shown in FIGS. 7 and 8, a controller 526 can be provided to activate the motor(s) which drive(s) the rollers 518 and 512. In this example, the controller 526 senses the number of rotations of the particle removal roller 502 via a sensor. Once a predetermined number of rotations is reached, the controller 526 transmits a signal to the motor to begin rotation of the shafts 519 and 525 and to thereby cause movement of the rollers 518 and 512 and movement of the tape 514. (Alternatively, the controller 526 could produce this signal after a predetermined amount of time has past or after a predetermined usage of the system 500 is sensed.) The torque produced by the rotations will overcome the force of the biasing member 520 and move the rollers 512 to the contacting position of FIG. 8. The controller 526 can continue the cleaning for a predetermined period of time or for a predetermined number of rotations. Then, the controller 526 can cease the production of the activation signal to cause the rotation of the rollers 512 and 518 and movement of the tape 514 to cease, to cause the contact roller 512 to move back to the non-contacting position of FIG. 7 via the force of the biasing member 520, and to thereby cease the cleaning of the particle removal roller 502. The controller 520 can include suitable circuitry, hardware and/or software to produce the motor activation signal at the desired time.

All publications and patent applications mentioned in the specification are indicative of the level of skill of those skilled in the art to which this invention pertains. The entire disclosures of all publications and patent applications mentioned herein are hereby incorporated herein by reference to the same extent as if each individual publication or patent application was specifically and individually indicated to be incorporated by reference.

It is intended that the description of the present invention provided above is but one embodiment for implementing the invention. While specific alternatives to steps of the invention have been described herein, additional alternatives not specifically disclosed but known in the art are intended to fall within the scope of the invention. Moreover, variations in the description likely to be conceived of by those skilled in the art still fall within the breadth and scope of the disclosure of the present invention. Thus, it is understood that other applications of the present invention will be apparent to those skilled in the art upon the reading of the described embodiment and a consideration of the appended claims and drawings.

What is claimed is:

1. A defect detection system, for use in an image processing system wherein the suitability of a film for processing is determined prior to scanning, the defect detection system comprising:
   a sensor for detecting one or more imperfections on the film; and
   a microprocessor connected to the sensor that determines an amount and extent of imperfections on the film based on one or more reference sensor readings, and enables a determination of whether remedial actions can be taken to make film having detected imperfections thereon suitable for processing.

2. The defect detection system as recited in claim 1, wherein the image processing system comprises a digital film processing system.

3. The defect detection system as recited in claim 1, further comprising an output device to report the amount and extent of imperfections on the film.

4. The defect detection system as recited in claim 1, further comprising a reference sensor and a memory, wherein the reference sensor readings are determined by the reference sensor and stored in the memory.

5. The defect detection system as recited in claim 1, wherein the sensor is a reflective sensor.

6. The defect detection system as recited in claim 1, wherein the sensor detects light transmitted through the film.

7. The defect detection system as recited in claim 1, further comprising a tape dispenser positioned to repair the film if the imperfection detected by the sensor is a breakage in the film.

8. The defect detection system as recited in claim 1, wherein the sensor detects the abnormalities in the shape of the perforations on the film.

9. The defect detection system as recited in claim 1, wherein the sensor detects moisture on the film.

10. The defect detection system as recited in claim 1, wherein the sensor detects oil on the film.

11. The defect detection system as recited in claim 1, wherein the
   sensor detects the moisture level of the film and if the moisture level is above a predetermined acceptable moisture level the film is dried until the moisture level drops below the predetermined acceptable moisture level.

12. The defect detection system as recited in claim 1, wherein the sensor detects foreign objects on the film.

13. The defect detection system as recited in claim 1, wherein the sensor detects foreign objects on the film and if the amount of foreign objects on the film is above a predetermined acceptable foreign object level the film is cleaned until the foreign object level drops below the predetermined acceptable foreign object level.

14. A defect detection system for use in image processing system, the defect detection system comprising:
   a roller for feeding a film into a sensor;
   a reflective sensor for detecting imperfections on a film;
   a microprocessor connected to the sensor that determined an amount and extent of imperfections on the film and compares the determined amount and extent of imperfections to reference sensor readings; and
   a router for separating film that is suitable for film processing from film that is not suitable for film processing based on a comparison of actual sensor readings to reference sensor readings by the microprocessor.

15. The defect detection system as recited in claim 14, further comprising an output device to report the amount and extent of imperfections on the film.

16. The defect detection system as recited in claim 14, further comprising a reference sensor and a memory, wherein the reference sensor readings are determined by the reference sensor and stored in the memory.

17. The defect detection system as recited in claim 14, further comprising a tape dispenser positioned to repair the film if the imperfection detected by the sensor is a breakage in the film.

18. The defect detection system as recited in claim 14, wherein the sensor detects the moisture level of the film.

19. The defect detection system as recited in claim 14, wherein the sensor detects the moisture level of the film and if the moisture level is above a predetermined acceptable moisture level the film is dried until the moisture level drops below the predetermined acceptable moisture level.

20. The defect detection system as recited in claim 14, wherein the sensor detects foreign objects on the film.

21. The defect detection system as recited in claim 14, wherein the sensor detects foreign objects on the film and if the amount of foreign objects on the film is above a predetermined acceptable foreign object level the film is cleaned until the foreign object level drops below the predetermined acceptable foreign object level.

22. A method of identifying film suitable for digital image processing, the method comprising the steps of:
   exposing a film to one or more light sources;
   detecting light reflected from the film to measure imperfections on the film;
   determining if the measured imperfections on the film exceed reference sensor readings; and
   routing the film based on the sensor output depending on whether the film is suitable for digital film processing from film that is not suitable for digital film processing.

23. Me method as recited in claim 22, further comprising the step of correcting the imperfection on the film by selecting a remedial measure that corrects the imperfection.

24. The method as recited in claim 23, wherein the remedial measure comprises the step of removing excessive moisture from the film.

25. The method as recited in claim 23, wherein the remedial measure comprises the step of removing foreign objects from the film.

26. The method as recited in claim 23, wherein the remedial measure comprises the step of repairing one or more broken sprocket holes are repaired prior to digital film processing.

27. The method as recited in claim 23, wherein the steps of exposing the film to one or more light sources, detecting the light reflected from the film to measure imperfections on the film, determining if the imperfections on the film exceed reference sensor readings, and correcting the imperfection on the film are repeated in an iterative manner.

28. The method as recited in claim 22, further comprising the steps of:
   determining the level of moisture in the film;
   detecting foreign objects on the film; and
   scanning for one or more broken sprocket holes on edges of the film, wherein an imperfection in the moisture level, a presence of foreign objects and broken sprocket holes will lead to rejection of the film from further digital film processing.

29. The method as recited in claim 22, further comprising the step of rolling the film into a canister when the film is not suitable for digital film processing.

30. The method as recited in claim 22, further comprising the step of reporting one or more reasons why the film is not suitable for digital film processing.

31. The method as recited in claim 30, wherein the one or more reasons identify an imperfection type and a location on the film where the imperfection was detected.

32. The method as recited in claim 22, further comprising the step of cleaning the film before the step of exposing the film to one or more light sources.

33. An imaging system comprising:
   a defect detector comprising a defect sensor for detecting one or more imperfections on a photographic media, and a microprocessor connected to the defect sensor that determines an amount and extent of imperfections on the photographic media based on one or more reference sensor readings, said sensor and said microprocessor further enabling a determination of whether remedial measures can be taken to the media to make it suitable for image processing based on the amount and extent of determined imperfections as compared to the reference sensor readings;
   at least one light source operable to illuminate the photographic media; and
   at least one image sensor operable to detect light from the photographic media.

* * * * *